United States Patent
Cardoso et al.

(10) Patent No.: US 9,567,626 B2
(45) Date of Patent: Feb. 14, 2017

(54) MONOLITHIC DEVICE COMBINING CMOS WITH MAGNETORESISTIVE SENSORS

(71) Applicant: MAGNOMICS, S.A., Cantanhede (PT)

(72) Inventors: Filipe Arroyo Cardoso, Lisbon (PT); Tiago Miguel Lopes Marta da Costa, Tucifal (PT); José António Henriques Germano, Sacavém (PT); Moisés Simões Piedade, Paço de Arcos (PT)

(73) Assignee: MAGNOMICS, S.A., Cantanhede (PT)

( * ) Notice: Subject to any disclaimer, the term of this patent is extended or adjusted under 35 U.S.C. 154(b) by 0 days.

(21) Appl. No.: 14/323,640

(22) Filed: Jul. 3, 2014

(65) Prior Publication Data

US 2014/0323337 A1  Oct. 30, 2014

Related U.S. Application Data

(63) Continuation of application No. PCT/IB2013/000397, filed on Jan. 4, 2013.

(51) Int. Cl.
  *G01N 27/72* (2006.01)
  *C12Q 1/68* (2006.01)
  (Continued)

(52) U.S. Cl.
  CPC .......... *C12Q 1/6825* (2013.01); *G01N 27/745* (2013.01); *G01N 33/54326* (2013.01);
  (Continued)

(58) Field of Classification Search
  CPC . G01N 27/72; G01N 27/745; G01N 33/54326
  See application file for complete search history.

(56) References Cited

U.S. PATENT DOCUMENTS 5,981,297 A    11/1999  Baselt
6,057,167 A     5/2000  Shieh et al.
(Continued)

FOREIGN PATENT DOCUMENTS

EP    1469311 A1    10/2004
EP    1659405 A1     5/2006
(Continued)

OTHER PUBLICATIONS

Germano, Jose et al.; "A Portable and Autonomous Magnetic Detection Platform for Biosensing"; Sensors, vol. 9; May 27, 2009; pp. 4119-4137, ISSN: 1424-8220.
(Continued)

*Primary Examiner* — Erik B Crawford
(74) *Attorney, Agent, or Firm* — Husch Blackwell LLP

(57) ABSTRACT

A monolithic device comprises a substrate. An array of sensing elements is coupled to the substrate, and each sensing element includes a magnetoresistive sensor. An analog electric drive generator is coupled to the substrate, and the electric drive generator produces a sensor-biasing signal that biases the magnetoresistive sensors of the array. An analog multiplexer is coupled to the substrate, and outputs of the array are coupled to inputs of the multiplexer. An analog signal conditioning circuit is coupled to the substrate, wherein at least one output of the multiplexer is coupled to at least one input of the signal conditioning circuit. The monolithic device is fabricated using both complementary metal-oxide semiconductor (i.e., CMOS) technology and thin film technology. For example, the electric drive generator, the multiplexer, and the signal conditioning circuit may be fabricated with CMOS technology, while the magnetoresistive sensors of the array are fabricated with thin film technology.

25 Claims, 9 Drawing Sheets

(51) Int. Cl.
  *G01N 33/543* (2006.01)
  *G01N 27/74* (2006.01)
  *G01R 33/09* (2006.01)
  *G01N 35/00* (2006.01)

(52) U.S. Cl.
  CPC . *G01N 33/54333* (2013.01); *G01N 33/54373* (2013.01); *G01R 33/091* (2013.01); *G01N 2035/00158* (2013.01)

(56) References Cited

U.S. PATENT DOCUMENTS

| | | |
|---|---|---|
| 6,518,747 B2 | 2/2003 | Sager et al. |
| 7,048,890 B2 | 5/2006 | Coehoorn et al. |
| 7,106,051 B2 | 9/2006 | Prins et al. |
| 7,504,262 B2 | 3/2009 | Fox |
| 7,977,937 B2 | 7/2011 | Voegeli |
| 8,053,244 B2 | 11/2011 | Ryan et al. |
| 8,084,270 B2 | 12/2011 | Prins et al. |
| 8,093,897 B2 | 1/2012 | Pan |
| 8,133,439 B2 | 3/2012 | Wang et al. |
| 8,283,912 B2 | 10/2012 | Nieuwenhuis et al. |
| 8,334,147 B2 | 12/2012 | Voegeli |
| 8,436,436 B2 | 5/2013 | Solin et al. |
| 8,447,379 B2 | 5/2013 | Flynn |
| 8,557,608 B2 | 10/2013 | Bangert |
| 8,586,385 B2 | 11/2013 | Su et al. |
| 8,614,572 B2 | 12/2013 | Florescu et al. |
| 8,790,916 B2 | 7/2014 | Achrol et al. |
| 8,797,028 B2 | 8/2014 | Verschuren et al. |
| 8,822,227 B2 | 9/2014 | Kahlman |
| 8,828,740 B2 | 9/2014 | Kahlman et al. |
| 8,945,946 B2 | 2/2015 | Ikeda |
| 8,993,236 B2 | 3/2015 | Hajimiri et al. |
| 9,023,651 B2 | 5/2015 | Evers et al. |
| 9,103,824 B2 | 8/2015 | Ovsyanko |
| 9,103,843 B2 | 8/2015 | Nieuwenhuis et al. |
| 9,157,891 B2 | 10/2015 | Ovsyanko et al. |
| 2006/0194327 A1* | 8/2006 | Kahlan ............. G01N 15/0656 436/86 |
| 2007/0264159 A1 | 11/2007 | Graham et al. |
| 2007/0298510 A1 | 12/2007 | Imamura et al. |
| 2008/0024118 A1 | 1/2008 | Kahlman et al. |
| 2008/0218165 A1* | 9/2008 | Kahlman ......... G01N 33/54326 324/260 |
| 2008/0246470 A1 | 10/2008 | Kahlman et al. |
| 2008/0309323 A1 | 12/2008 | Okano et al. |
| 2008/0309329 A1 | 12/2008 | Kahlman et al. |
| 2009/0102465 A1 | 4/2009 | Jansen et al. |
| 2009/0102472 A1 | 4/2009 | Nieuwenhuis et al. |
| 2009/0152657 A1 | 6/2009 | Suh et al. |
| 2009/0184706 A1 | 7/2009 | Duric et al. |
| 2009/0186420 A1 | 7/2009 | Kahlman et al. |
| 2009/0206832 A1 | 8/2009 | Kahlman et al. |
| 2009/0219012 A1 | 9/2009 | Nieuwenhuis et al. |
| 2009/0243594 A1 | 10/2009 | Kahlman |
| 2009/0251136 A1 | 10/2009 | Prins et al. |
| 2009/0278534 A1 | 11/2009 | Kahlman |
| 2009/0280571 A1 | 11/2009 | Nieuwenhuis et al. |
| 2009/0309588 A1 | 12/2009 | Nieuwenhuis et al. |
| 2009/0317915 A1 | 12/2009 | Han et al. |
| 2010/0052665 A1 | 3/2010 | Van Den Homberg et al. |
| 2010/0136669 A1 | 6/2010 | Weekamp et al. |
| 2010/0148765 A1 | 6/2010 | Nieuwenhuis et al. |
| 2010/0148768 A1 | 6/2010 | Schwarz |
| 2010/0176807 A1 | 7/2010 | Duric et al. |
| 2010/0188076 A1 | 7/2010 | Kahlman et al. |
| 2010/0194386 A1* | 8/2010 | Prins ................ G01N 33/54333 324/228 |
| 2010/0248973 A1 | 9/2010 | Van Lankvelt et al. |
| 2010/0253323 A1 | 10/2010 | De Theije et al. |
| 2010/0273269 A1 | 10/2010 | Van Lankvelt et al. |
| 2010/0277160 A1 | 11/2010 | De Theije et al. |
| 2010/0279887 A1 | 11/2010 | Lee et al. |
| 2010/0289483 A1 | 11/2010 | Immink et al. |
| 2010/0291710 A1 | 11/2010 | Ovsyanko et al. |
| 2010/0311186 A1 | 12/2010 | Gregory et al. |
| 2010/0323355 A1 | 12/2010 | Dittmer |
| 2010/0330698 A1 | 12/2010 | Evers |
| 2011/0014719 A1 | 1/2011 | Sijbers et al. |
| 2011/0027916 A1 | 2/2011 | Nieuwenhuis |
| 2011/0206560 A1 | 8/2011 | Neijzen et al. |
| 2011/0241664 A1 | 10/2011 | Zhang |
| 2013/0124101 A1 | 5/2013 | Eckert |
| 2013/0163140 A1 | 6/2013 | Ovsyanko |
| 2013/0217584 A1 | 8/2013 | Zhang et al. |
| 2014/0014506 A1 | 1/2014 | Dimitrov |
| 2014/0097829 A1 | 4/2014 | Wang et al. |
| 2014/0178900 A1 | 6/2014 | Jung et al. |
| 2014/0193851 A1* | 7/2014 | Hayden .................. B03C 1/01 435/29 |
| 2014/0266186 A1 | 9/2014 | Osterfeld et al. |
| 2014/0292318 A1 | 10/2014 | Wang et al. |
| 2015/0044778 A1 | 2/2015 | Wang et al. |
| 2015/0050721 A1 | 2/2015 | Asogawa et al. |
| 2015/0051102 A1 | 2/2015 | Fu et al. |
| 2015/0093750 A1 | 4/2015 | Ovsyanko et al. |
| 2015/0226732 A1 | 8/2015 | De Theije et al. |
| 2015/0233908 A1 | 8/2015 | Kelly et al. |
| 2015/0247821 A1 | 9/2015 | Enpuku et al. |

FOREIGN PATENT DOCUMENTS

| | | |
|---|---|---|
| EP | 2018537 | 11/2007 |
| EP | 2027468 | 11/2007 |
| EP | 1982768 A2 | 10/2008 |
| WO | 2005116661 A1 | 12/2005 |
| WO | 2006080571 A1 | 8/2006 |
| WO | 2008044162 A2 | 4/2008 |
| WO | 2008107847 A1 | 9/2008 |
| WO | 2008111013 A2 | 9/2008 |
| WO | 2009024922 A2 | 2/2009 |
| WO | 2009081336 A1 | 7/2009 |
| WO | 2009083856 A2 | 7/2009 |
| WO | 2010013169 A1 | 2/2010 |
| WO | 2010086772 A1 | 8/2010 |
| WO | 2012053851 A1 | 4/2012 |
| WO | 2013071910 A1 | 5/2013 |
| WO | 2014111187 A1 | 7/2014 |
| WO | 2014189624 A1 | 11/2014 |

OTHER PUBLICATIONS

Gaster, Richard S. et al.; "nanoLAB: An Ultraportable, Handheld Diagnostic Laboratory for Global Health"; Lab on a Chip, vol. 11; Jan. 1, 2011; XP055065318.

Han, Shu-Jen et al.; "CMOS Integrated DNA Microarray Based on GMR Sensors"; Electron Devices Meeting, 2006, IEDM '06, IEEE, PI; Dec. 1, 2006; pp. 1-4, XP031078300.

Cardoso, F. et al.; "Diode/Magnetic Tunnel Junction Cell for Fully Scalable Matrix-Based Biochip"; Journal of Applied Physics, American Institute of Physics, vol. 99, No. 8; Apr. 19, 2006; XP012084239, ISSN: 0021-8979.

Cardoso, F. et al.; "Noise Characteristics and Particle Detection Limits in Diode+MTJ Matrix Elements for Biochip Applications"; IEEE Transactions on Magnetics, vol. 43, No. 6; Jun. 1, 2007; pp. 2403-2405, XP011181555, ISSN: 0018-9464.

Xu, Liang et al.; "Giant Magnetoresistive Sensors for DNA Microarray"; IEEE Transactions on Magnetics, vol. 44, No. 11; Nov. 1, 2008; pp. 3989-3991, XP011240260, ISSN: 0018-9464.

Cardoso, F. et al.; "Integration of Magnetoresistive Biochips on a CMOS Circuit", IEEE Transactions on Magnetics, vol. 48, No. 11; Nov. 1, 2012; pp. 3784-3787, XP011468652, ISSN: 0018-9464.

Van Kerckhoven, Ilse; Notification of Transmittal of the International Search Report and the Written Opinion of the International Searching Authority, date of mailing Jun. 12, 2013, for International Application No. PCT/IB2013/000397, filed Jan. 4, 2013; European Patent Office; Rijswijk, Netherlands.

Zwerger, Markus; International Search Report, date of mailing Oct. 4, 2013, for International Application No. PCT/IB2013/000397, filed Jan. 4, 2013; European Patent Office; Rijswijk, Netherlands.

(56) References Cited

OTHER PUBLICATIONS

Zwerger, Markus; Written Opinion of the International Preliminary Examining Authority, date of mailing Mar. 5, 2014, for International Application No. PCT/IB2013/000397, filed Jan. 4, 2013; European Patent Office; Rijswijk, Netherlands.

Paredes Sanchez; Notification of Transmittal of the International Preliminary Report on Patentability, date of mailing May 15, 2014, for International Application No. PCT/IB2013/000397, filed Jan. 4, 2013; European Patent Office; Rijswijk, Netherlands.

Rui Pereira Bento; Search report dated Mar. 1, 2012 for Portuguese provisional patent application No. 106084, National Industrial Property Institute (INPI), Portugal; see in particular p. 3.

Adrega, T. et al.; "Thin-Film Silicon MEMS DNA Sensors"; Journal of Non-Crystalline Solids, vol. 352; Apr. 19, 2006; ISSN: 0022-3093.

Leitao, Jose et al.; "Scalable and High Throughput Biosensing Platform"; 2013 IEEE, 2013 23rd International Conference on Field Programmable Logic and Applications (FPL) Sep. 2-4, 2013.

A.G. da Cunha Ferreira; Arguments in Support of Demand filed for International Application No. PCT/IB2013/000397, dated May 5, 2014.

\* cited by examiner

US 9,567,626 B2

MONOLITHIC DEVICE COMBINING CMOS WITH MAGNETORESISTIVE SENSORS

CROSS REFERENCE TO RELATED APPLICATIONS

This application is a bypass continuation of International Application No. PCT/IB2013/000397, filed Jan. 4, 2013, entitled "MONOLITHIC DEVICE COMBINING CMOS WITH MAGNETORESISTIVE SENSORS", which claims the benefit of Portuguese Provisional Patent Application Serial No. 106084, filed Jan. 4, 2012, entitled "A MONOLITHIC DEVICE COMBINING CMOS WITH MAGNETORESISTIVE SENSORS", the disclosures of which are hereby incorporated by reference.

BACKGROUND

The present disclosure relates in general to magnetoresistive sensors and more specifically to sensing magnetic fields, temperature, a presence of a target species in a sample, etc., using magnetoresistive sensors.

Miniaturized instruments using biochips or lab-on-a-chip technologies coupled to high sensitivity signal detectors, powerful signal and control processors, and associated high level software intelligent systems, are likely to envisage handheld microsystems for biological, clinical, or chemical analysis. Applications for such handheld microsystems include DNA sequence detection for genetic disease diagnostics, mutation detection or gene expression quantification, and antibody-antigen interaction detection for disease diagnostics (e.g., cancer, virus, auto-immune diseases, etc.), bacteriological characterization of a sample (e.g., water, food, etc.), analysis of toxins (e.g., water, meat, milk, etc.), etc.

A typical biochip consists of a set of biological probes, a hybridization chamber with a microfluidic channel arrangement, target biomolecules, label molecules (e.g., a fluorescent type of molecule such as fluorophore labels that can be attached to the target), and a hybridization detection mechanism that can be integrated on chip or be placed externally.

BRIEF SUMMARY

According to aspects of the present disclosure, a monolithic device is disclosed. The monolithic device may be used in applications such as detecting a presence of a target species, or more generally, for sensing magnetic fields, temperature, or both. The monolithic device comprises an array of sensing elements, an analog electric drive generator, an analog multiplexer and optionally, an analog signal conditioning circuit, that together form a monolithic integrated circuit on a substrate. Each sensing element of the array of sensing elements includes a magnetoresistive sensor. Further, the electric drive generator produces a sensor-biasing signal that biases the magnetoresistive sensors of the array. Moreover, outputs of the array are coupled to inputs of the multiplexer and an output of the multiplexer may be coupled to an input of the signal conditioning circuit.

According to further aspects of the disclosure, a system is provided. The system may be used in applications such as detecting a presence of a target species, or more generally, for sensing magnetic fields, temperature, or both. The system comprises a monolithic device and a processing device coupled to the monolithic device. The monolithic device may be the monolithic device set out above. The processing device is programmed to receive the output of the monolithic device, e.g., from the signal conditioning circuit and to calculate a presence of the target species based at least in part on the output of the signal conditioning circuit.

According to still further aspects of the present disclosure, a method is provided. The method may be implemented for applications such as detecting a presence of a target species in a sample. The method comprises providing a monolithic device having an array of sensing elements, an analog electric drive generator, an analog multiplexer and an analog signal conditioning circuit that together form a monolithic integrated circuit on a substrate. Each sensing element of the array of sensing elements includes a magnetoresistive sensor. Further, the electric drive generator produces a sensor-biasing signal that biases the magnetoresistive sensors of the array. Moreover, outputs of the array are coupled to inputs of the multiplexer and an output of the multiplexer is coupled to an input of the signal conditioning circuit.

The method may further comprise utilizing labeling molecules of the target species in the sample with magnetizable label particles and generating a magnetic field. The method may also further include attracting the molecules of the target species to the binding molecules of the monolithic device using the magnetic field and attaching the molecules of the target species to the binding molecules of the monolithic device. The unbound particles are removed. Further the method may comprise magnetizing the magnetizable label particles attached to the binding molecules, where the magnetizable label particles are attached to the binding molecules via the molecules of the target species. Moreover, the method may include sensing the magnetized label particles with the array of sensing elements and calculating a presence of the target species in the sample based at least in part on the sensed magnetized label particles.

DETAILED DESCRIPTION

Various aspects of the present disclosure relate to a monolithic device that is fabricated using a combination of complementary metal-oxide semiconductor (i.e., CMOS) technology and thin film technology. More particularly, device fabrication utilizes CMOS technology for matrix commutation, sensor biasing, multiplexing, and signal conditioning and amplification. Correspondingly, device fabrication utilizes thin film technology for the fabrication of magnetoresistive sensors, magnetic field generating structures or both.

Magnetoresistive sensors, which detect a magnetic field change created by magnetically labeled molecules, may be used to detect a presence of a target species. In these systems, fluorophore labels are replaced by magnetic labels (e.g., non-remanent ferromagnetic particles, paramagnetic particles, etc.), and detection is performed using highly sensitive, magnetic field sensors. Markers (i.e., label particles) are specifically attached to the target molecules, and the magnetic stray field of the label particles is detected by a magnetoresistive sensor as a change of the sensor's electrical resistance.

Magnetic biosensors exhibit relatively high molecular detection resolution, high sensitivity and the direct availability of an electronic signal suitable for further automated processing and analysis. For instance, measured signals for the detection of DNA-strands show that the magnetic biosensors are more sensitive than current fluorescent detection units.

Accordingly, various aspects of the present disclosure further relate to the use of the monolithic device described above, in combination with a processing device and other optional components to derive systems and methods for detecting a presence of a target species in addition to, or alternatively to sensing magnetic fields, temperature, or both.

Figure 1:
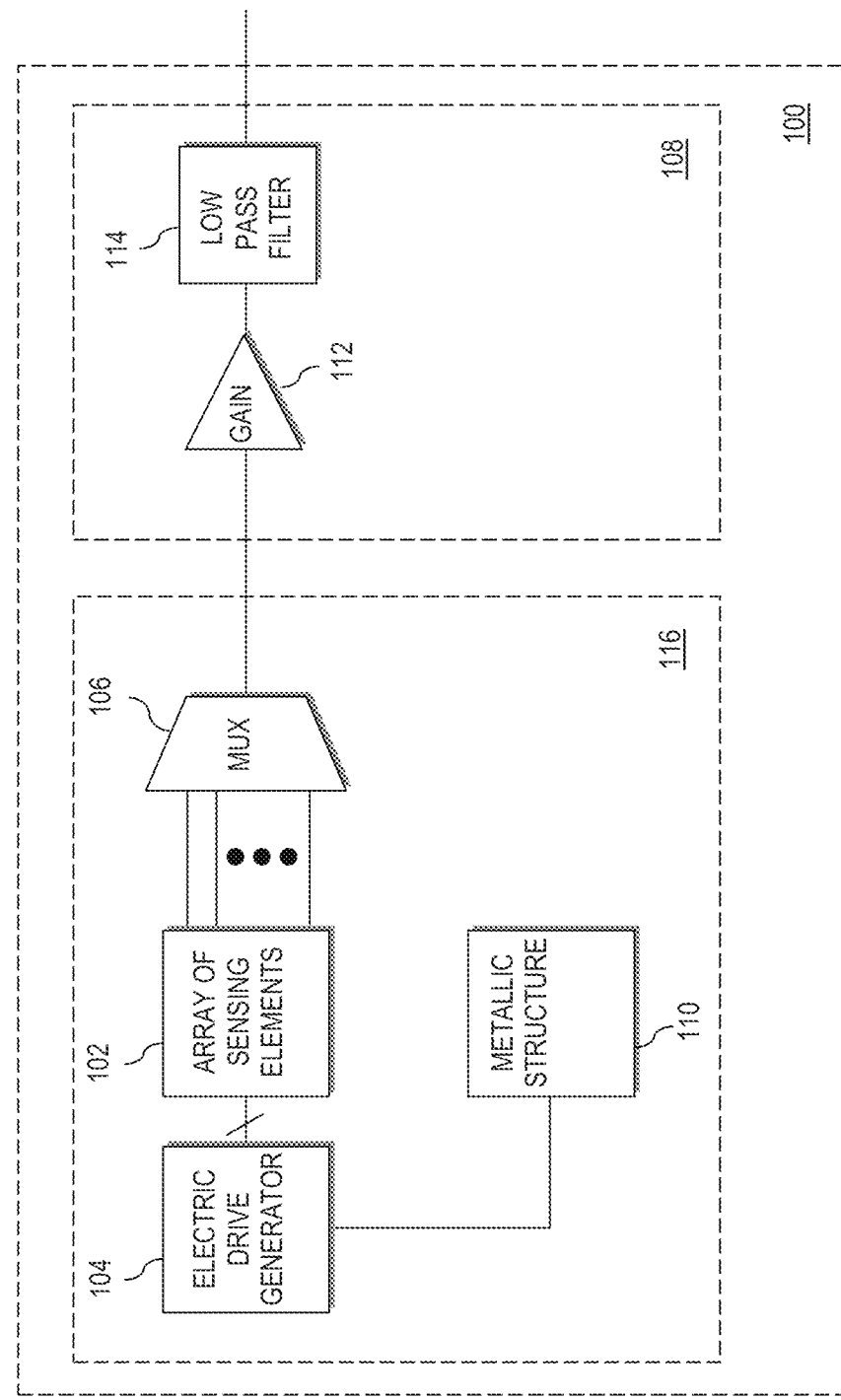
FIG. 1 is a block diagram illustrating a monolithic device, according to various aspects of the present disclosure.

Turning now to the figures and specifically to FIG. 1, a block diagram of a monolithic device 100 is shown. The monolithic device 100 includes an array 102 of sensing elements; an analog electric drive generator 104; an analog multiplexer 106; and an analog signal conditioning circuit 108. In some embodiments, the monolithic device 100 further includes a metallic structure 110 that generates a magnetic field, as will be described in greater detail herein.

The array 102 is arranged generally in a matrix of rows and columns of sensing elements, where each sensing element includes a magnetoresistive sensor, as will be described in greater detail herein.

The analog electric drive generator 104 produces a sensor-biasing signal that biases the magnetoresistive sensors of the array 102. In various embodiments, the analog electric drive generator 104 also produces a driving signal that drives the metallic structure 110 to produce a magnetic field, to heat the device, or both. In practice, the analog electric drive generator 104 may be a static generator (i.e., always produces the same signal(s)) or a configurable generator (i.e., changes the signal(s) depending on a user input). Also, the electric drive generator 104 may generate a drive current as an alternating current (i.e., AC) or direct current (i.e., DC).

The analog multiplexer 106 has inputs that are coupled to outputs of the array 102. Thus, the array 102 feeds analog signals to the analog multiplexer. The analog multiplexer takes those analog signals from the array 102 and determines which signal to place on an output of the multiplexer 106. The selection of which analog signal to pass to the output of the multiplexer 106 may be performed serially or in parallel and is performed based on time-division multiplexing. In an illustrative implementation, over a predetermined period of time, an analog signal output from each of the magnetoresistive sensors of array 102 is eventually passed to the output of the analog multiplexer 106.

The signal conditioning circuit 108 couples to the analog multiplexer 106 such that the output of the analog multiplexer 106 feeds an input of the signal conditioning circuit 108. The signal conditioning circuit 108 can provide signal gain/level adjustment, signal conditioning or both to condition a signal for further processing. For instance, the signal conditioning circuit 108 illustrated in FIG. 1, includes an amplifier 112 (e.g., a linear low-noise amplifier) and a filter 114, e.g., a low pass filter. However, in practice, the signal conditioning circuit 108 need not comprise both an amplifier 112 and a filter 114. Moreover, in illustrative implementations, the gain of the amplifier 112 includes a programmable gain and can be set to decouple the signal from the multiplexer 106. The filter 114 can be used to suppress any interference and limit the bandwidth required for further processing.

In an illustrative implementation, the monolithic device 100 is fabricated using both CMOS technology and thin film technology. For example, the magnetoresistive sensors of the array 102 are fabricated with thin film technology. Correspondingly, the analog electric drive generator 104, the analog multiplexer 106, and the analog signal conditioning circuit 108 are fabricated with CMOS technology. Moreover, CMOS technology may be utilized for matrix commutation, e.g., to transfer the sensor-biasing signal of the electric drive generator 104 to one or more inputs to the array 102, to transfer signals from the outputs of the array 102 to the multiplexer 106, or both. In embodiments that incorporate the metallic structure 110, the metallic structure 110 can be fabricated using thin film technology, using CMOS technology, or both.

In operation of the exemplary embodiment of FIG. 1, the analog electric signal generator 104 biases the magnetoresistive sensors of the array 102. The outputs of the array 102 feed the inputs to the multiplexer 106, which time-multiplexes the signals to pass one signal at a time to the signal conditioning circuit 108. The signal conditioning circuit 108, which includes the amplifier 112 and the low pass filter 114, produces a resulting filtered signal that is provided as an output that can be propagated off of the monolithic device 100 for further processing.

In embodiments with the metallic structure 110 (e.g., the embodiment of FIG. 1), in general, when the drive signal from the electric drive generator 104 drives the metallic structure 110, the metallic structure 110 generates a magnetic field that encompasses the sensing elements of the array 102. As noted above, this drive current may be alternating current (i.e., AC) or direct current (i.e., DC).

Moreover, the generated magnetic field can be used to implement different functions at different times during operation. As such, the metallic structure 110 may be implemented in practice, as one or more components that may be coupled or independent. For instance, the metallic structure 110 may be used to generate a homogeneous magnetic field, a magnetic field gradient, or both. As such, the metallic structure 110 can include a gradient magnetic field generator, a homogeneous magnetic field generator, or both (as described in greater detail in reference to FIGS. 4-8). Each generator may be implemented as an independent metallic component of the metallic structure 110, or two or more generators may be coupled or otherwise implemented by the same metallic component of the metallic structure 110. Further, the metallic structure 110 may also generate heat to heat the monolithic device 100 to a predetermined temperature.

Figure 2:
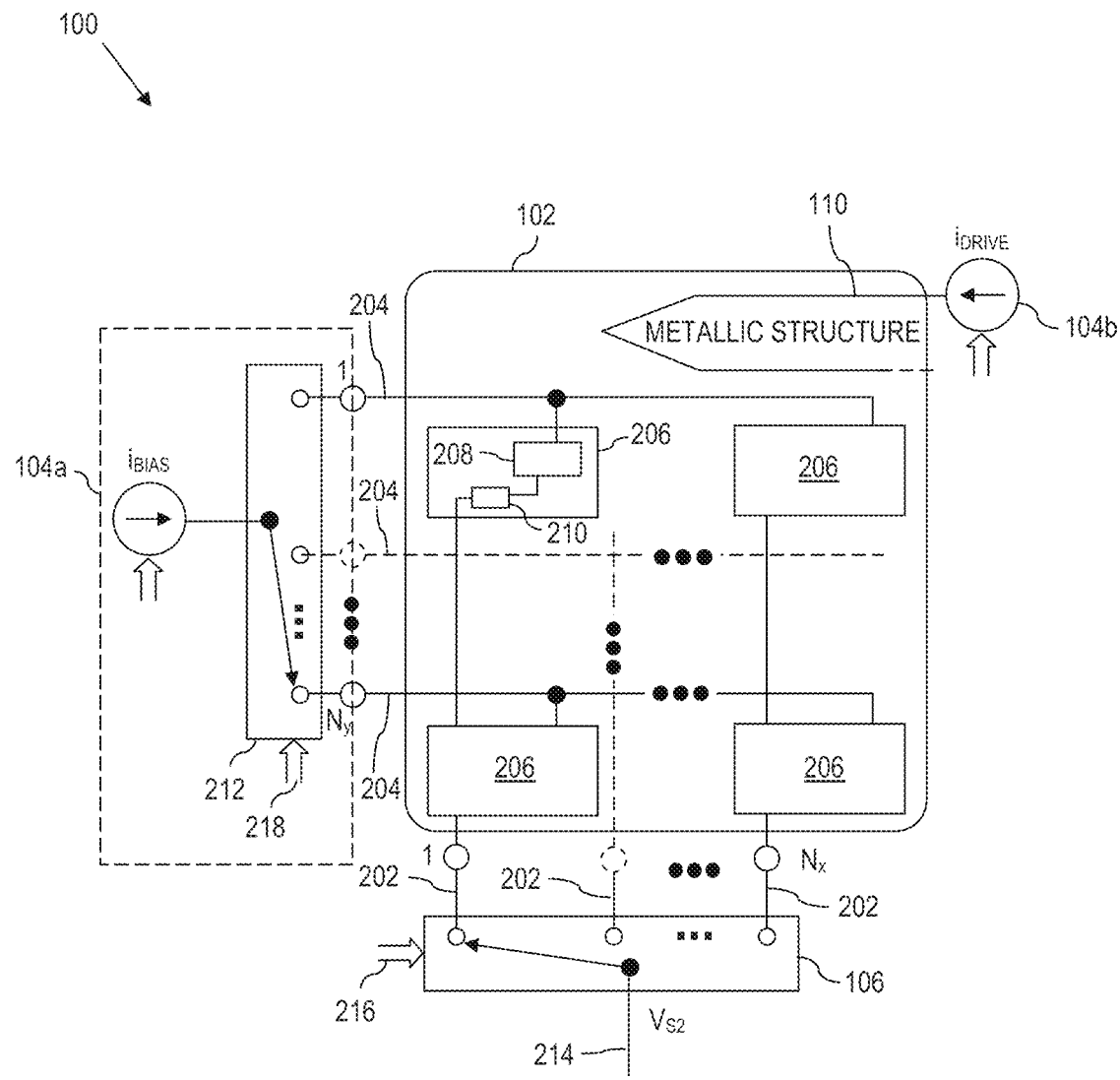
FIG. 2 is a schematic illustrating a portion of the monolithic device of FIG. 1 including an array of magnetoresistive sensors, an analog electric drive generator, a multiplexer, and a metallic structure, according to various aspects of the present disclosure.

The array 102 of sensing elements, electric drive generator 104, multiplexer 106, and metallic structure 110 encompass a front end 116 of the monolithic device, which is described in greater detail in reference to FIG. 2.

Referring now to FIG. 2, a schematic of the front end 116 of the monolithic device 100 is shown. The front end 116 includes the array 102 of sensing elements, the electric drive generator (shown schematically as two current sources, labeled 104a, 104b), the multiplexer 106, and the metallic structure 110. The exemplary array 102 of sensing elements is arranged into columns 202 and rows 204. As shown, the array 102 includes $N_x$ columns and $N_y$ rows.

At intersections of rows 204 and columns 202, the array 102 includes a sensing element 206. Each sensing element 206 includes a magnetoresistive sensor 208 and a switching device 210. The switching device 210 couples the associated magnetoresistive sensor 208 to the sensing element's 206 corresponding column 202. For example, the switching device 210 may be a diode or a transistor with the transistor's gate tied to the transistor's source. Moreover, the switching device 210, the magnetoresistive sensor 208, the metallic structure 110, or combinations thereof or associations of these elements may be used as a localized temperature sensor where temperature is related to a signal passed by the switching device 210.

The magnetoresistive sensor 208 is a transducer whose electrical resistance changes, e.g., linearly, with an applied magnetic field. When biased by a sensor-biasing signal $i_{BIAS}$, which is supplied by the analog electric drive generator 104, the magnetoresistive sensor 208 produces an analog voltage signal, e.g., proportional to the sensed magnetic field. The magnetoresistive sensors 208 may be of any appropriate technology including, but not limited to: Anisotropy Magneto Resistance (i.e., AMR), Giant Magneto Resistance (i.e., GMR) or Magnetic Tunneling Junction (i.e., MTJ).

In operation, the electric drive generator 104a generates the sensor-biasing signal $i_{BIAS}$. A demultiplexer (i.e., demux) 212 places the sensor-biasing signal $i_{BIAS}$ on a row 204 of the array 102, which feeds all of the sensing elements 206 on that row 204. The magnetoresistive sensors 208 of the sensing elements 206 drive their corresponding switching devices 210, which pass signals resulting from the sensor 208 to the columns 202 of the array 102. However, when a row 204 is not being driven by the electric drive generator 104a, the signals from those sensors 208 are not strong enough to pass through the switching device 210 to drive the columns 202. Thus, each column 202 is only being driven by one sensing element 206 at a time. Although the demux 212 is shown for purposes of clarity of discussion as part of the analog electric drive generator 104, the demux 212 may be placed in other positions on the device 100. Moreover, in certain implementations, the demux 212 may be unnecessary, or its function may be implemented in other suitable manners.

The columns 202 feed the outputs of the array 102, which feed the inputs to the multiplexer 106. The output of the multiplexer 106 is taken at the output line 214. The multiplexer 106 cycles through each of the columns 202 (e.g., column 1-column $N_x$) over time, e.g., in succession. While reading the columns 1-$N_x$, the electric drive generator 104 may hold the signal $i_{BIAS}$ constant for the currently selected row 204. After all of the columns 202 are cycled through, the demux 212 passes the sensor-biasing signal $i_{BIAS}$ to the next row 204 of the array 102, and the multiplexer 106 cycles through the columns 202 again to read all of the sensors 208 of that row 204. Thus, over time, a signal from every magnetoresistive sensor 208 (e.g., every magnetoresistive sensor addressed by rows 1-$N_y$ and columns 1-$N_x$) is passed out of the front end 116 via output line 214 to the signal conditioning circuit (108, FIG. 1) and eventually off of the monolithic device 100. As illustrated, the multiplexer 106 is controlled by control lines 216 and the demux 212 is controlled by control lines 218 to facilitate the desired time multiplexing scheme. In illustrative implementations, Time Division Multiple Access (TDMA) is utilized in such a way as to allow the reduction of the non-linear response of the multiplexing circuit analog signal with the signal to be multiplexed.

To create the magnetic field, the electric drive generator 104 creates a drive signal $i_{DRIVE}$, (schematically represented by the current source 104b) which feeds the metallic structure 110. As such, the electric drive generator 104 may be one component that produces two signals $i_{BIAS}$ and $i_{DRIVE}$ or the electric drive generator 104 may be comprised of two or more components 104a, 104b, each producing a signal $i_{BIAS}$, $i_{DRIVE}$ respectively.

Moreover, as will be described more fully herein, the metallic structure 110 may include different components, e.g., one or more magnetic gradient generators integrated into the monolithic device, a homogenous field generator integrated into the monolithic device or combinations thereof. As such, in practice, the electric drive generator 104 may actually generate one or more $i_{DRIVE}$ signals. For instance, a first $i_{DRIVE}$ signal can be generated for the homogenous field generator. A second $i_{DRIVE}$ signal can be generated for the magnetic gradient generator(s). Also, where multiple magnetic gradient generators are implemented, a separate $i_{DRIVE}$ signal can be generated for each magnetic gradient generator, or a single $i_{DRIVE}$ signal can be generated to drive multiple magnetic gradient generators. Each $i_{DRIVE}$ signal can be implemented from a single analog electric drive generator 104, or multiple analog electric drive generators 104 can be implemented on the monolithic device to generate each $i_{DRIVE}$ signal.

Figure 3:
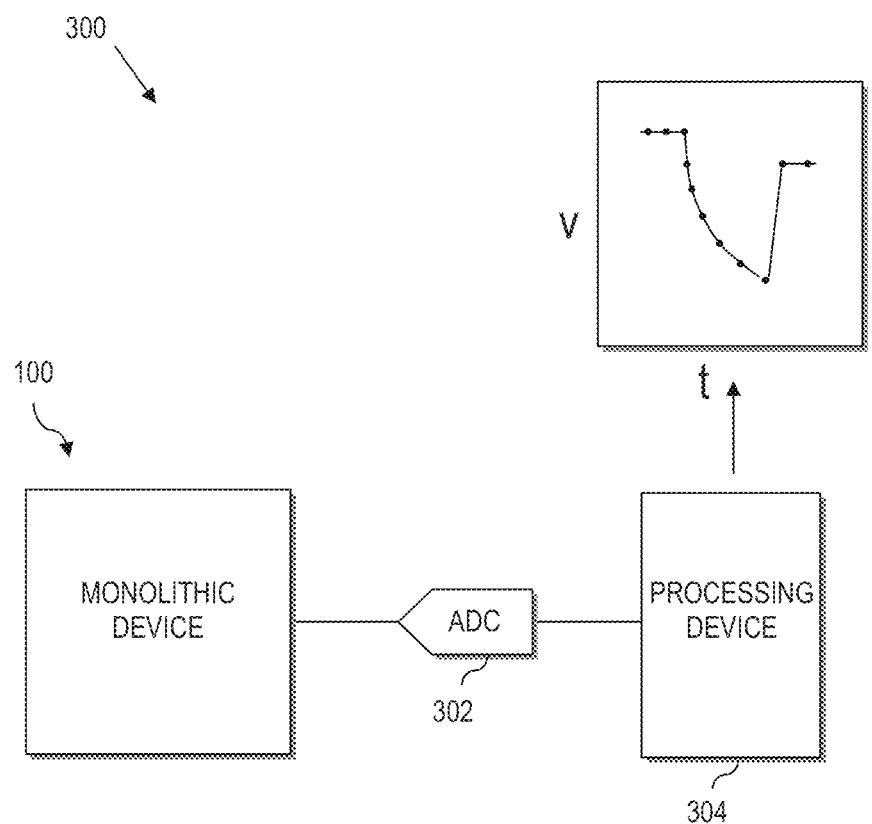
FIG. 3 is a block diagram illustrating a system including the monolithic device of FIGS. 1-2, according to various aspects of the present disclosure.

Turning now to FIG. 3, the monolithic device 100 is shown in a system 300 for detecting a presence of a target species in a sample. The monolithic device 100 is coupled to an analog-to-digital converter (i.e., ADC) 302, which converts the analog output from the monolithic device 100 to digital signals. For example, the ADC 302 may convert the analog output to a serial digital signal or a parallel signal. The ADC 302 feeds a processing device 304. The processing device 304 may be any device including but not limited to a processor, microprocessor, microcontroller, a programmable complex logic (CPLD), a field programmable gate array (FPGA), etc. Further, the processing device may be implemented using more than one device (e.g., a processor and an FPGA, etc). Thus, the processing device 304 receives the output of the signal conditioning circuit of the monolithic device 100. The processing device 304 calculates the presence of the target species based at least in part on the received output of the signal conditioning circuit of the monolithic device 100.

Figure 4:
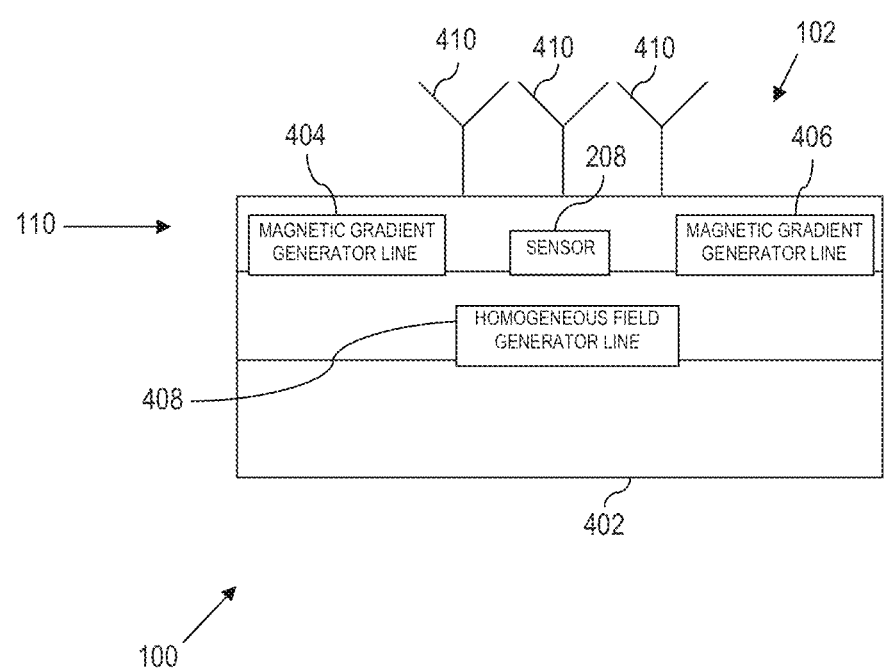
FIG. 4 is a block diagram illustrating the monolithic device of FIGS. 1-2 with binding molecules, according to various aspects of the present disclosure.

Turning now to FIGS. 4-8, a method of using the monolithic device 100 to detect a presence of a target species is shown. In FIG. 4, the monolithic device 100 includes a substrate 402. The components 102, 104, 106, 108, 110 of FIG. 1, are coupled to the substrate 402 to form a monolithic integrated circuit on the substrate 402 to define the monolithic device 100 in a manner analogous to that described above with reference to FIGS. 1-3. In the exemplary embodiments of FIGS. 4-8, the metallic structure 110 includes two opposite gradient magnetic field generator lines 404, 406 and a homogeneous magnetic field generator line 408. The magnetoresistive sensor 208 of the array 102 is shown between the opposite gradient magnetic field generator lines 404, 406 and above the homogeneous magnetic field generator line 408.

Binding molecules 410 are attached to the monolithic device 100, and those binding molecules 410 selectively bind to molecules of the target species. The binding molecules 410 may be antibodies of the target species. Further, different types of binding molecules may be attached in groups to the surface of the device 100. For example, binding molecules for different target species may be attached to each sensor 208 or group of sensors on the device 100. Thus, a multitude of target species may be detected with one monolithic device.

Figure 5:
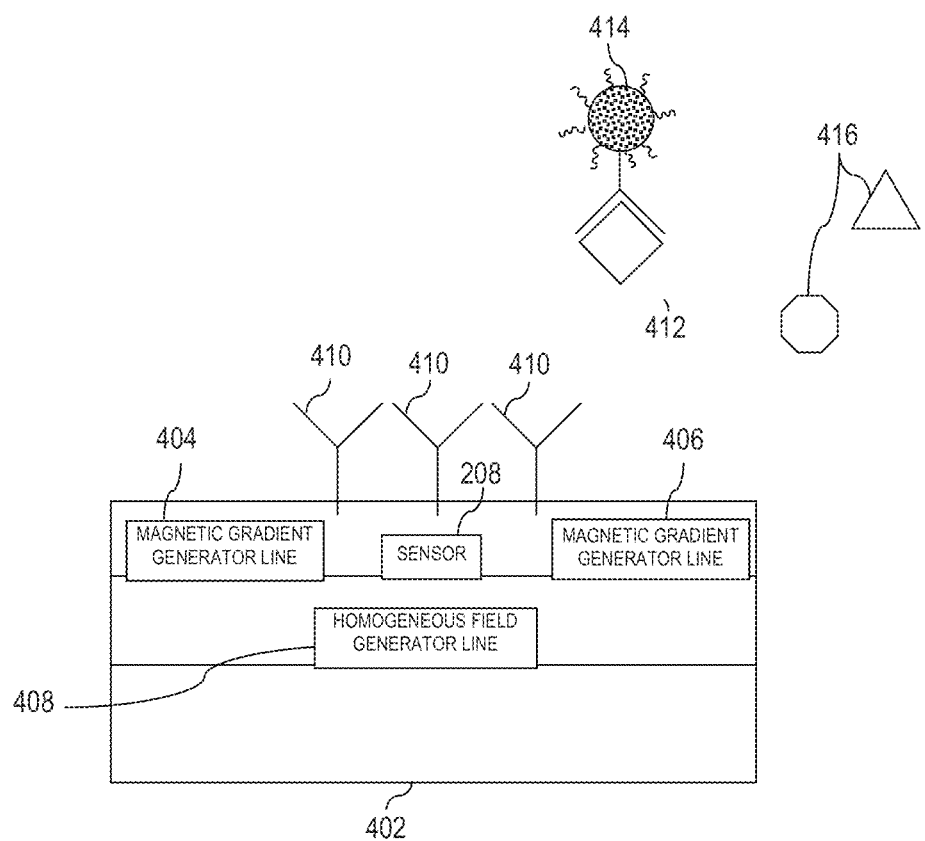
FIG. 5 is a block diagram illustrating the monolithic device of FIG. 4 and a magnetizable label particle attached to a molecule of a species of interest, according to various aspects of the present disclosure.

Turning now to FIG. 5, molecules 412 of the target species are labeled with magnetizable label particles 414. However, molecules 416 that are not of the target species are not labeled.

Figure 6:
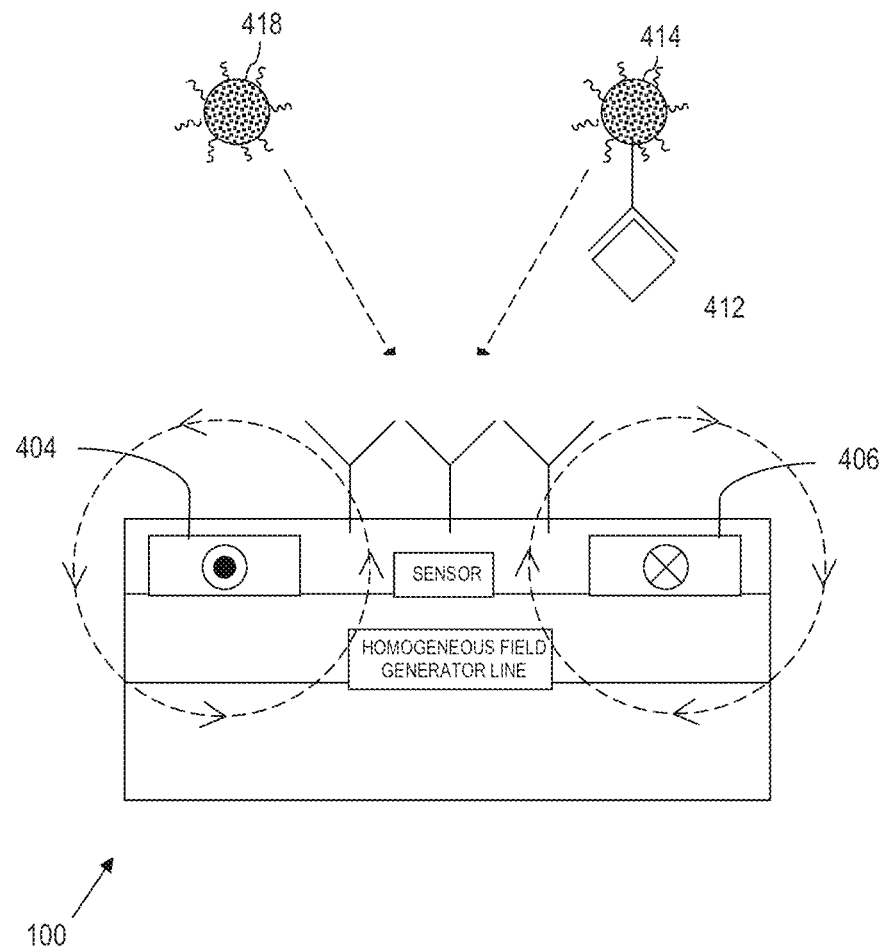
FIG. 6 is a block diagram illustrating the monolithic device of FIGS. 4-5 attracting the molecules of the target species to the binding molecules, according to various aspects of the present disclosure.

Referring to FIG. 6, the gradient magnetic field generator lines 404, 406 are activated with a suitable $i_{DRIVE}$ signal to generate a magnetic field gradient, which attracts both the label particles 414 with labeling molecules 412 of the target species and unbound label particles 418 to the binding molecules 410 on the monolithic device 100. As noted above, each magnetic field generator line 404, 406 may be driven by the same $i_{DRIVE}$ signal, or each magnetic field generator line 404, 406 may be driven by a separate $i_{DRIVE}$ signal. An external magnetic field generator (not shown) may be used to supplement the gradient magnetic field generator lines 404, 406.

Figure 7:
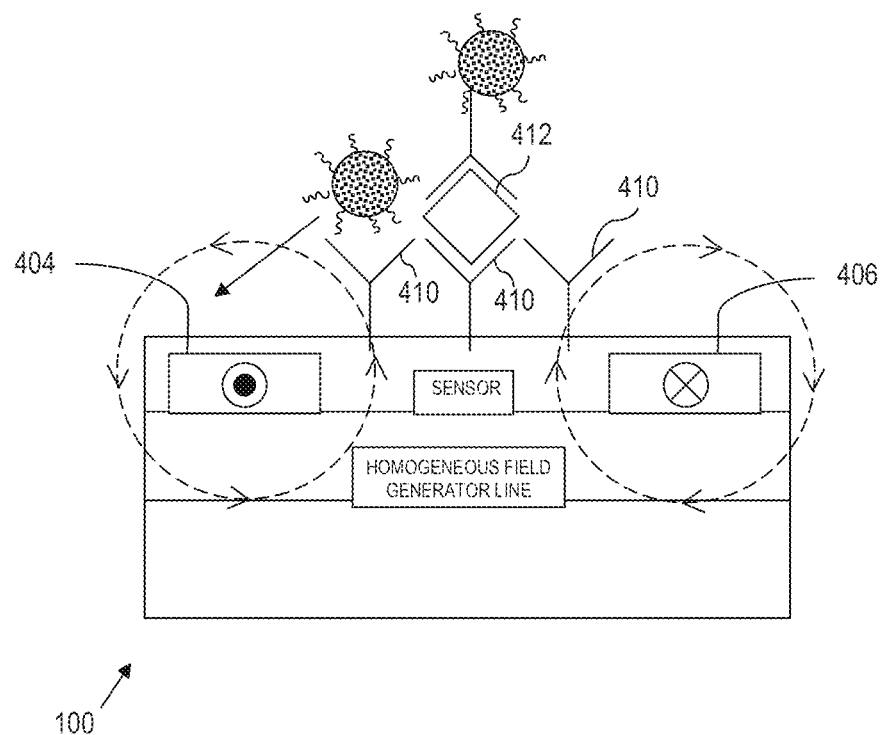
FIG. 7 is a block diagram illustrating the monolithic device of FIGS. 4-6 attaching the molecules of the target species to the binding molecules and removing the unbound particles, according to various aspects of the present disclosure.

Turning to FIG. 7, the labeled molecules 412 of the target species attach to the binding molecules 410. Any unbound label particles 418 are removed. For example, the unbound label particles 418 may be removed by: passing a washing solution in a microfluidic channel (not shown) of the monolithic device 100, using the magnetic field gradient to propel the unbound label particles 418 away from the sensor 208, or both, and therefore, the removed particles will not be magnetized and detected.

Figure 8:
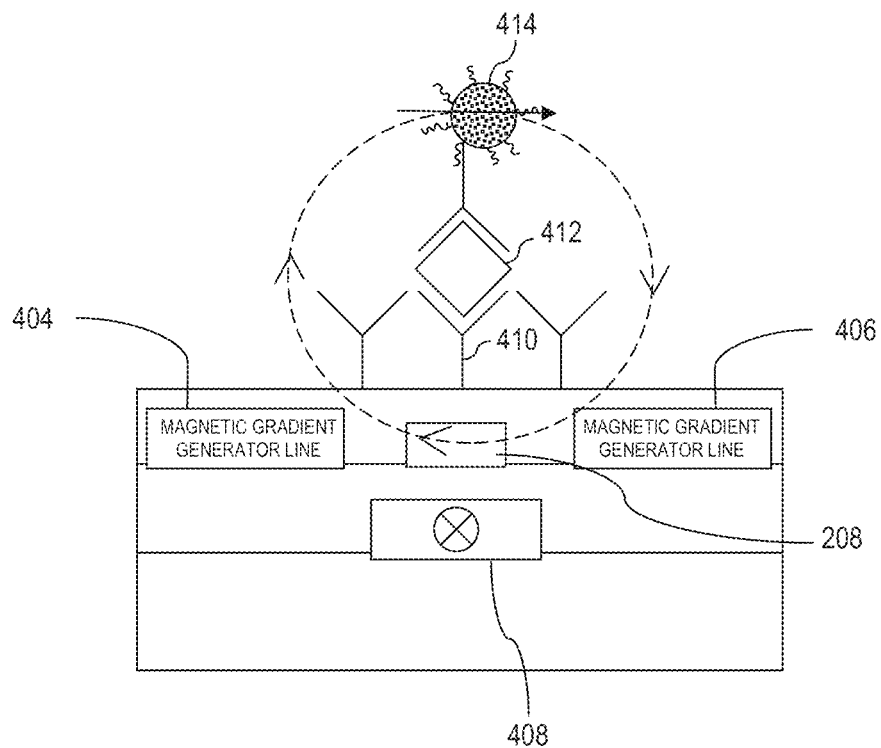
FIG. 8 is a block diagram illustrating the monolithic device of FIGS. 4-7 with attached, magnetized label-particles affecting the magnetoresistive sensor of the monolithic device, according to various aspects of the present disclosure.

In FIG. 8, the gradient magnetic field generator lines 404, 406 are deactivated, and the homogeneous magnetic field generator line 408 is activated to generate a homogeneous magnetic field that magnetizes the magnetizable label particle 414 bound to the molecule 412 of the target species attached to the binding molecule 410. The magnetized label particle 414 then produces a magnetic field, which is sensed by the magnetoresistive sensor 208. That sensor 208 produces a signal that, in conjunction with other magnetoresistive sensors in the array, are sent to the processing device (e.g., 304 of FIG. 3), which uses the signals to determine the presence of the target species.

An external magnetic field generator (not shown) may be used to supplement the gradient magnetic field generator lines 404, 406, the homogeneous magnetic field generator line 408, or both.

Figure 9:
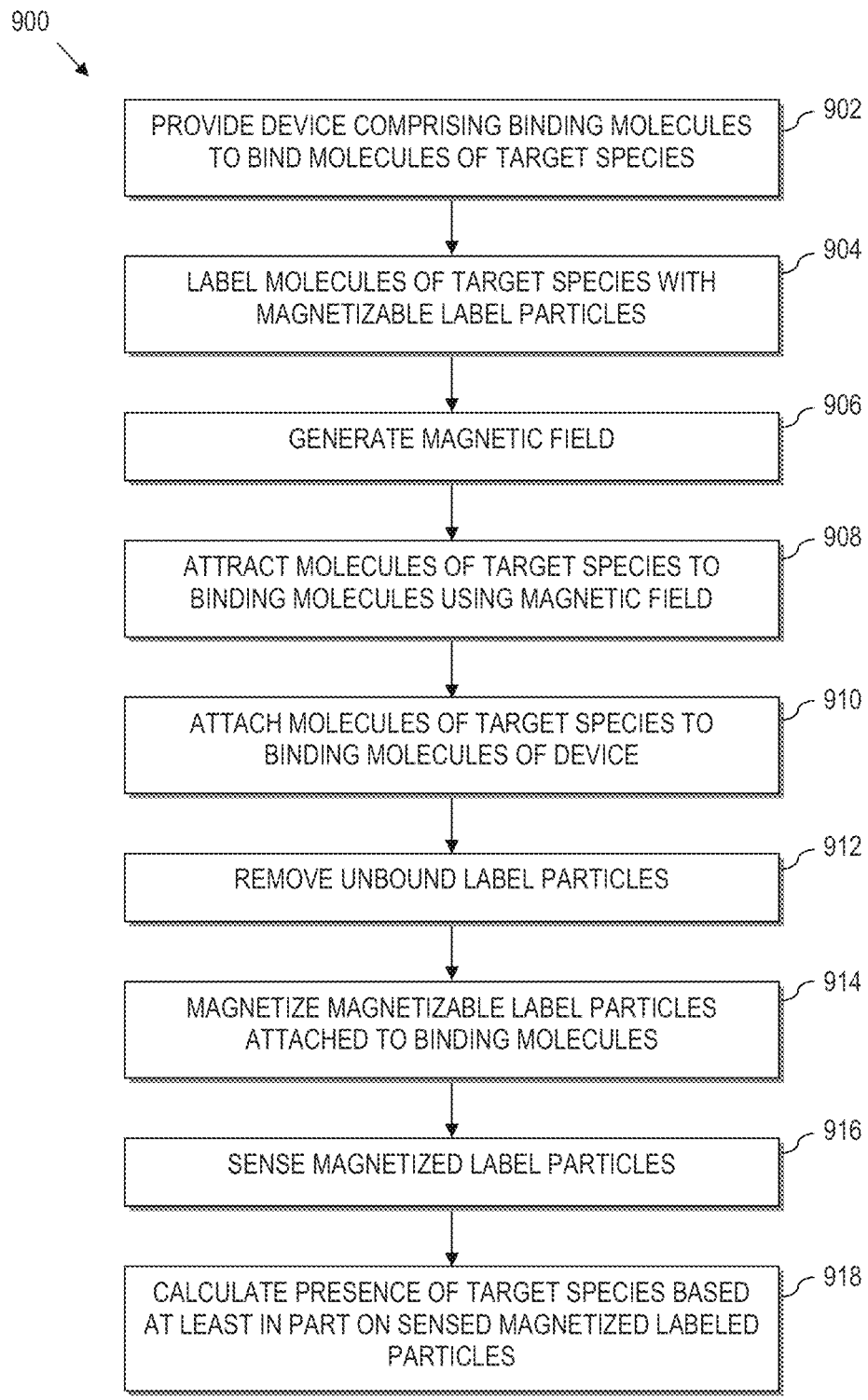
FIG. 9 is a flow chart illustrating a method for detecting a presence of a target species in a sample using the monolithic device of FIG. 1, according to various aspects of the present disclosure.

FIG. 9 is a flow chart illustrating a method 900 for detecting a presence of a target species in a sample using the monolithic device 100. At 902, a monolithic device (100 of FIG. 4) is provided. The monolithic device comprises binding molecules (410 of FIG. 4) to bind molecules of a target species. For example, the binding molecules can be antibodies of the target species. Thus, the molecules of the target species can bind to the monolithic device, yet other molecules will not bind to the monolithic device.

At 904, molecules of the target species in the sample are labeled with magnetizable label particles. At 906, the gradient magnetic field generator lines of the monolithic device generate a magnetic field gradient. The magnetic field gradient may be supplemented by a magnetic field generator located external to the monolithic device.

That magnetic field gradient attracts the label particles toward the device at 908; thus, the molecules of the target species are attracted to the binding molecules of the monolithic device. At 910, the molecules of the target species attach to the binding molecules of the monolithic device.

At 912, any unbound label particles are removed. For example, the unbound label particles may be removed by: passing a washing solution in a microfluidic channel of the monolithic device, using the magnetic field gradient to propel the unbound label particles away from the monolithic device, or both. The label particles that are attached to the binding molecules via the molecules of the target species (i.e., the label particles that remain after the unbound label particles are removed) are magnetized at 914. Those magnetized label particles produce a magnetic field that is sensed by magnetoresistive sensors of the monolithic device at 916.

The magnetoresistive response of the magnetoresistive sensors is monitored, and the monitored response is used to calculate the presence and concentration of the target species within the sample at 918. To calculate the presence of the target species based at least in part on the sensed magnetized label particles, the analog electric drive generator biases the sensors of the sensing elements. The demultiplexer selects a row to of sensing elements to bias, and the multiplexer selects a column passing a signal. The signal conditioning circuit conditions the resulting signal and passes the conditioned signal to the processor. There, the processing device uses a received series of the received signal over time to calculate the presence, concentration, or both of the target species in the sample.

The method 900 may be performed under a controlled temperature or with a sequence of different controlled temperatures. To control the temperature to a predetermined temperature, the metallic structure of the monolithic device heats the monolithic device 100 (e.g., from the current supplied by the electric drive generator) and the switching device 210, the magnetoresistive sensor 208, the metallic structure 110, or a combination thereof are used as temperature sensors.

The monolithic device 100 may be used in a multitude of applications requiring the detection of very weak magnetic fields by a high number of sensors. The usage of a single monolithic device combining CMOS technology with highly sensitive thin film magnetoresistive sensors has the advantage of reducing the electromagnetic interferences between the sensors and the other electronics (e.g., mux, demux, electric drive generator, signal conditioning circuit, etc.), which improves the signal-to-noise ratio of resulting signals, and enables the electronics to be tailored to the specific needs of each application. Furthermore, the monolithic device is suitable for portable devices since it allows the fabrication of a small device with a high density of sensors which requires few external electronic components.

An example application of the monolithic device is the detection of biomolecular recognition. As explained above, the monolithic device detects magnetically labeled target molecules which will specifically attach to molecules of a target species previously attached on different spots of the device surface. Then, after removing unbound particles using a microfluidic system, a magnetic field from the metallic structures fabricated in the device, other methods, or combinations thereof, the remaining magnetic labels are detected using a magnetoresistive sensor.

The method can be applied to different kind of molecules enabling a large spectrum of applications such as biomedical, food, veterinary and public health industries. In most of these applications, a large number of molecules need to be detected. The monolithic device and methods described herein supply high sensitivity sensors, quick assay speed, and portability, which are very important characteristics when detecting these types of molecules. Therefore, the present disclosure is suitable for these applications since the monolithic device described more fully herein provides high sensor density, improved signal to noise ratios thus high sensitivity, reduced number of external devices needed, small size of the device, etc.

According to further aspects of the present disclosure, the monolithic device may comprise at least one magnetoresistive sensor array and corresponding driving and reading circuits. As described more fully herein, CMOS technology is used to implement a circuit to digitally address, drive, control and read the signals from the sensing elements that are placed over the CMOS post-processed circuit. Thin Film technology is used to realize magnetoresistive sensors comprised in each sensing elements.

Each sensor array features a scalable architecture in a matrix configuration with sensing elements addressable by its position in the matrix. Signal conditioning is performed in the monolithic device by a low noise amplifier and by a set of filters. The resulting signal is digitized and processed to extract the sensed magnetic fields and/or temperature.

The flowchart and block diagrams in the Figures illustrate the architecture, functionality, and operation of possible implementations of systems, methods and devices according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the invention in the form disclosed. Many modifications and variations will be apparent to those of ordinary skill in the art without departing from the scope and spirit of the disclosure. Aspects of the disclosure were chosen and described in order to best explain the principles of the disclosure and the practical application, and to enable others of ordinary skill in the art to understand the disclosure for various embodiments with various modifications as are suited to the particular use contemplated.

What is claimed is:

1. A monolithic device comprising:
a substrate;
an array of sensing elements coupled to the substrate, wherein each sensing element includes a magnetoresistive sensor and a switching device;
a metallic structure coupled to the substrate, wherein the metallic structure is driven by a driving signal to generate a magnetic field about the array of sensing elements;
an electric drive generator coupled to the substrate, wherein the electric drive generator produces a sensor-biasing signal that biases the magnetoresistive sensors of the array;
a multiplexer coupled to the substrate, wherein outputs of the array are coupled to inputs of the multiplexer through the corresponding switching device; and
a signal conditioning circuit coupled to the substrate, wherein an output of the multiplexer is coupled to an input of the signal conditioning circuit;
wherein the metallic structure includes two opposite magnetic field generator lines and a third magnetic field generator line arranged such that at least one of the magnetoresistive sensors of the array of sensing elements is between the opposite magnetic field generator lines and above the third magnetic field generator line; and
the array, the electric drive generator, the multiplexer and the signal conditioning circuit form a monolithic integrated circuit on the substrate.

2. The monolithic device of claim 1, wherein:
the array of sensing elements is arranged into columns and rows of sensing elements;
the magnetoresistive sensor of each sensing element is formed using thin film technology;
each switching device is implemented as a complementary metal-oxide semiconductor switching device that couples the corresponding magnetoresistive sensor to an associated column;
the magnetoresistive sensors formed using thin film technology are placed over the switching devices formed using complementary metal-oxide semiconductor technology;
the switching device couples the corresponding magnetoresistive sensor to an associated one of the columns;
the sensor-biasing signal drives a select one of the rows; and the columns of sensing elements along the selected one of the rows feed the outputs of the array of sensing elements.

3. The monolithic device of claim 1, wherein:
binding molecules are attached to the monolithic device;
the opposite magnetic field generator lines define at least one gradient magnetic field generator that generates a magnetic field gradient that attracts both bound and unbound magnetizable label particles to the binding molecules, wherein the bound magnetizable label particles are bound to molecules of at least one target species to form labeled molecules of the at least one target species that attach to the binding molecules, and the unbound magnetizable label particles are not bound to molecules of the at least one target species; and
the third magnetic field generator line comprises at least one homogeneous magnetic field generator that generates a homogeneous magnetic field that magnetizes the bound magnetizable label particles bound to the molecules of the at least one target species and attached to the binding molecules.

4. The monolithic device of claim 1, wherein:
the metallic structure heats the monolithic device; and
each switching device of the array, magnetoresistive sensor or metallic structure senses the temperature such that the sensed temperature is related to the corresponding switching device signal.

5. The monolithic device of claim 1, further comprising a further electric drive generator, wherein the further electric drive generator produces the driving signal that drives the metallic structure to produce a magnetic field.

6. The monolithic device of claim 1, wherein the sensor-biasing signal that biases the magnetoresistive sensors of the array is a desired sensor-biasing signal based on user input and the electric drive generator is configurable to produce the desired sensor-biasing signal.

7. The monolithic device of claim 1, wherein the multiplexer implements Time Division Multiple Access to choose a select input of the multiplexer to transfer to the output of the multiplexer.

8. The monolithic device of claim 1, wherein the signal conditioning circuit includes a linear low noise amplifier with a programmable gain and capable of decoupling the input signals.

9. The monolithic device of claim 1, wherein the signal conditioning circuit includes a low pass filter.

10. The monolithic device of claim 1 further comprising a microfluidic channel positioned above the array of sensing elements, the microfluidic channel configured for allowing a washing solution to remove unbound label particles.

11. The monolithic device of claim 1, wherein the monolithic device is incorporated into a system, further comprising:
a processing device coupled to the monolithic device, wherein the processing device is programmed to:
receive the output of the signal conditioning circuit; and
calculate a presence and concentration of molecules of at least one target species based at least in part on the output of the signal conditioning circuit.

12. A monolithic device comprising:
a substrate;
an array of sensing elements coupled to the substrate, wherein each sensing element includes a magnetoresistive sensor;
a metallic structure coupled to the substrate, wherein the metallic structure is driven by a driving signal to generate a magnetic field about the array of sensing elements;
a drive generator coupled to the substrate, wherein the drive generator produces a sensor-biasing signal that biases the magnetoresistive sensors of the array; and
an analog multiplexer coupled to the substrate, wherein outputs of the array are coupled to inputs of the multiplexer;
wherein:
the metallic structure includes two opposite magnetic field generator lines and a third magnetic field generator line arranged such that at least one of the magnetoresistive sensors of the array of sensing elements is between the opposite magnetic field generator lines and above the third magnetic field generator line; and
the array, the drive generator, and the multiplexer form a monolithic integrated circuit on the substrate.

13. The monolithic device of claim 12, wherein:
binding molecules are attached to the monolithic device;
the opposite magnetic field generator lines define at least one gradient magnetic field generator that generates a magnetic field gradient that attracts both bound and unbound magnetizable label particles to the binding molecules, wherein the bound magnetizable label particles are bound to molecules of at least one target species to form labeled molecules of the at least one target species that attach to the binding molecules, and the unbound magnetizable label particles are not bound to molecules of the at least one target species; and
the third magnetic field generator line comprises at least one homogeneous magnetic field generator that generates a homogeneous magnetic field that magnetizes the bound magnetizable label particles bound to the molecules of the at least one target species and attached to the binding molecules.

14. A method for determining a presence of molecules of at least one target species in a sample, the method comprising:
providing a monolithic device comprising:
a substrate;
an array of sensing elements coupled to the substrate, wherein each sensing element includes a magnetoresistive sensor and a switching device, and wherein binding molecules that selectively bind to molecules of the at least one target species are attached to the array of sensing elements;
a metallic structure coupled to the substrate, wherein the metallic structure is driven by a driving signal to generate a magnetic field about the array of sensing elements;
an electric drive generator coupled to the substrate, wherein the electric drive generator produces a sensor-biasing signal that biases the magnetoresistive sensors of the array;
a multiplexer coupled to the substrate, wherein outputs of the array are coupled to inputs of the multiplexer; and
a signal conditioning circuit coupled to the substrate, wherein an output of the multiplexer is coupled to an input of the signal conditioning circuit and the signal conditioning circuit produces an output based at least in part on the input of the signal conditioning circuit;
wherein:

the metallic structure includes two opposite gradient magnetic field generator lines and a homogeneous magnetic field generator line arranged such that at least one of the magnetoresistive sensors of the array of sensing elements is between the opposite gradient magnetic field generator lines and above the homogeneous magnetic field generator line; and the array, the electric drive generator, the multiplexer and the signal conditioning circuit form a monolithic integrated circuit on the substrate;

introducing the sample to the monolithic device, such that a response of the sensing elements is effected by binding of the at least one target species to the binding molecules;

determining the presence of the molecules of the at least one target species in the sample based on the effected response from the sensing elements.

15. The method of claim 14, further comprising:

labeling the molecules of the at least one target species in the sample with the magnetizable label particles;

generating a magnetic field by driving the metallic structure;

attracting the labeled molecules of the at least one target species to the binding molecules of the monolithic device using the magnetic field;

attaching the labeled molecules of the at least one target species to the binding molecules of the monolithic device;

removing unbound magnetizable label particles;

magnetizing the magnetizable label particles attached to the binding molecules, wherein the magnetizable label particles are attached to the binding molecules via the molecules of the at least one target species;

sensing the attached magnetized label particles with the array of sensing elements; and wherein said determining the presence of the molecules of the at least one target species in the sample is based at least in part on the sensed magnetized label particles.

16. The method of claim 15, wherein generating a magnetic field includes generating the magnetic field at least from the metallic structure integrated in the monolithic device, wherein the metallic structure is driven by a further electric drive generator.

17. The method of claim 15, further comprising:

heating the monolithic device; and sensing a temperature of the device;

wherein determining the presence of the molecules of the at least one target species further comprises determining the presence of the molecules of the at least one target species in the sample based at least in part on the sensed temperature.

18. The method of claim 15, wherein sensing the attached magnetized label particles with the array of sensing elements comprises:

selecting an output of the array with the multiplexer to generate an output signal; and conditioning the output signal from the multiplexer with the signal conditioning circuit.

19. The method of claim 15, wherein removing unbound label particles comprises passing a washing solution in a microfluidic channel positioned above the array of sensors of the monolithic device such that the unbound label particles are removed.

20. The method of claim 15, wherein removing unbound label particles comprises using the magnetic field to propel the unbound label particles away from the monolithic device.

21. The monolithic device of claim 1, wherein:

the electric drive generator is an analog electric drive generator;

the multiplexer is an analog multiplexer; and the signal conditioning circuit is an analog signal conditioning circuit.

22. The monolithic device of claim 1, wherein the two opposite magnetic field generator lines and the third magnetic field generator line of the metallic structure are arranged so that each of the magnetoresistive sensors of the array of sensing elements are between the opposite magnetic field generator lines and above the third magnetic field generator line.

23. The monolithic device of claim 12, wherein the two opposite magnetic field generator lines and the third magnetic field generator line of the metallic structure are arranged so that each of the magnetoresistive sensors of the array of sensing elements are between the opposite magnetic field generator lines and above the third magnetic field generator line.

24. The method of claim 14, wherein:

the electric drive generator is an analog electric drive generator;

the multiplexer is an analog multiplexer; and the signal conditioning circuit is an analog signal conditioning circuit.

25. The method of claim 14, wherein the two opposite gradient magnetic field generator lines and the homogeneous magnetic field generator line of the metallic structure are arranged such that each of the magentoresistive sensors of the array of sensing elements are between the opposite gradient magnetic field generator lines and above the homogeneous magnetic field generator line.

* * * * *